United States Patent
Biedermann et al.

[11] Patent Number: 6,051,026
[45] Date of Patent: Apr. 18, 2000

[54] ALIGNMENT DEVICE FOR CONNECTING A STUMP SOCKET TO A PROSTHETIC LIMB

[75] Inventors: Lutz Biedermann, VS-Villingen; Wilfried Matthis, Weisweil; Markus Piro, Niedereschach, all of Germany

[73] Assignee: Biedermann Motech GmbH, Schwenningen, Germany

[21] Appl. No.: 09/070,643

[22] Filed: Apr. 30, 1998

[30] Foreign Application Priority Data

May 5, 1997 [DE] Germany ............ 197 18 580

[51] Int. Cl.[7] .................... A61F 2/80; A61F 2/74
[52] U.S. Cl. ........................ 623/38; 623/27
[58] Field of Search .......... 623/38, 36, 33, 623/27, 35, 16; 606/73, 59, 65, 72

[56] References Cited

U.S. PATENT DOCUMENTS

| | | | |
|---|---|---|---|
| 3,422,462 | 1/1969 | Finnieston | 623/38 |
| 5,116,382 | 5/1992 | Steinkamp et al. | 623/38 |
| 5,376,129 | 12/1994 | Faulkner et al. | 623/33 |
| 5,425,782 | 6/1995 | Phillips | 623/38 |
| 5,443,526 | 8/1995 | Hoerner | 623/38 |
| 5,464,443 | 11/1995 | Wilson et al. | 623/27 |
| 5,507,834 | 4/1996 | Laghi | 623/36 |
| 5,507,837 | 4/1996 | Laghi | 623/38 |
| 5,545,230 | 8/1996 | Kinsinger et al. | 623/38 |
| 5,746,773 | 5/1998 | Littig | 623/35 |
| 5,888,232 | 3/1999 | Taylor | 623/38 |
| 5,888,234 | 3/1999 | Littig | 623/38 |

FOREIGN PATENT DOCUMENTS

| | | | |
|---|---|---|---|
| 2 091 619 | 1/1972 | France | |
| 1 324 953 | 7/1973 | United Kingdom | |
| 2 162 069 | 1/1986 | United Kingdom | |
| 2162069 | 1/1986 | United Kingdom | 623/38 |

*Primary Examiner*—Mickey Yu
*Assistant Examiner*—Alvin Stewart
*Attorney, Agent, or Firm*—George W. Neuner; Dike, Bronstein, Roberts and Cushman LLP

[57] ABSTRACT

An alignment device connects a stump socket (1) to a prosthetic limb (21). The alignment device has an alignment member (8) with an opening (12) receiving a pin (7) connected to the stump socket (1). The size of the opening (12) is considerably greater than the cross-sectional dimension of the pin (7) and the pin can be locked in any position within the opening (12). This achieves a considerable improvement of the wear characteristics by lateral adjustment.

7 Claims, 4 Drawing Sheets

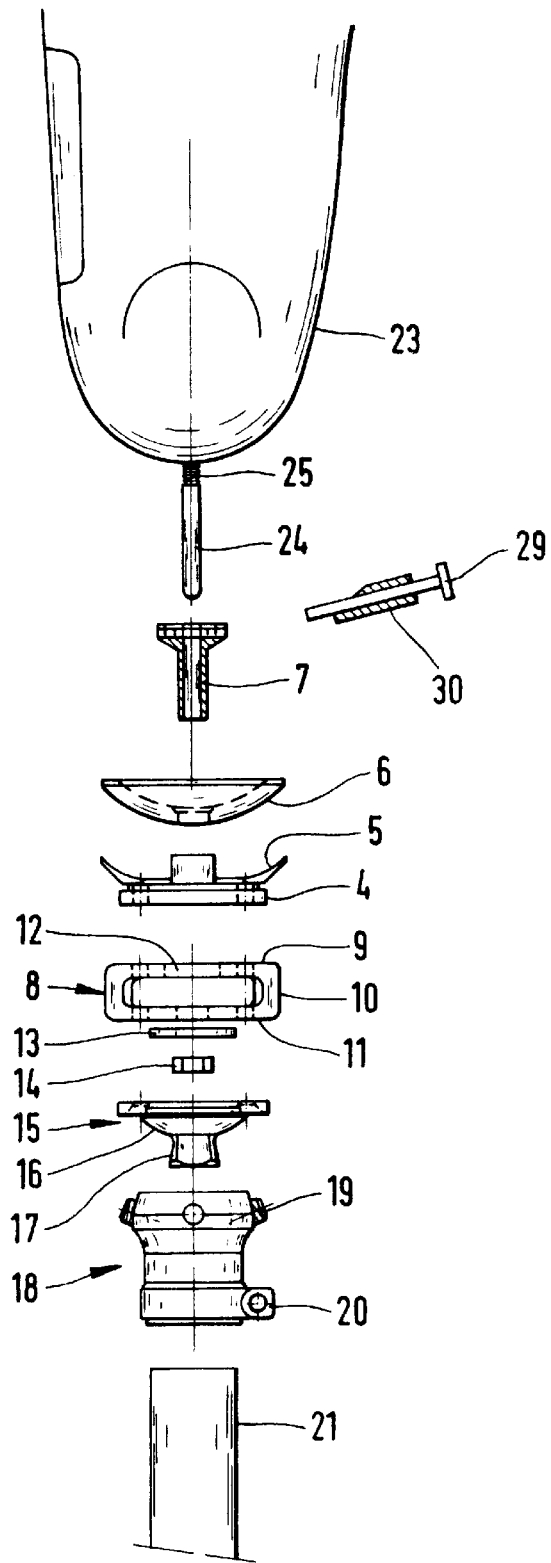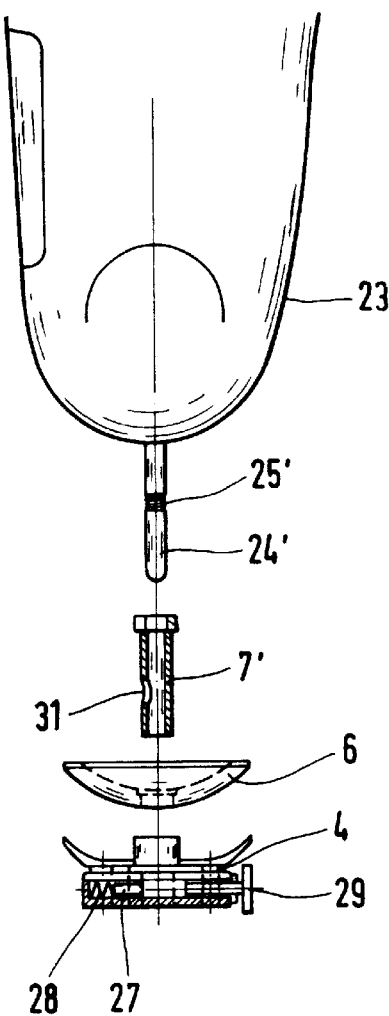

ALIGNMENT DEVICE FOR CONNECTING A STUMP SOCKET TO A PROSTHETIC LIMB

The invention relates to an alignment device for connecting a stump socket to a prosthetic limb according to the preamble of claim 1.

A stump socket is disclosed for example in U.S. Pat. No. 5,507,834. This socket is formed as a silicone socket liner which is pulled by the user over the residual limb to be connected to the prosthesis. The end of the liner to be connected to the residual limb comprises a pin which is formed as a bolt to be screwed into an alignment member of the prosthetic limb. The user takes care to wear the liner so that in a neutral, not-inclined position of the liner the pin extends in vertical direction and may therefore be inserted into a corresponding bore of the prosthetic limb. Here the problem arises that, although the pin extends in vertical direction, it is often not correctly positioned below the supporting point proper of the liner because of different forms of the legs, for example in case of knock-knees. Thus, difficulties arise for the user due to a considerable strain.

An alignment device is known from documents GB 2 162 069 A and U.S. Pat. No. 3,422,462.

It is the object of the invention to provide an alignment device as set out above which improves the connection of the stump socket to a prosthetic limb such that the wear conditions are considerably improved and a rapid and secure connection of a liner receiving the residual limb to the stump socket is enabled.

This object is achieved by an alignment device as defined in claim 1.

Further developments of the invention are defined in the subclaims.

Further features and advantages of the invention will be apparent from the description of an embodiment with reference to the figures. In the figures:

FIG. 2 shows the alignment device in exploded representation;

FIG. 3 shows a modified embodiment in exploded representation;

Figure 1:
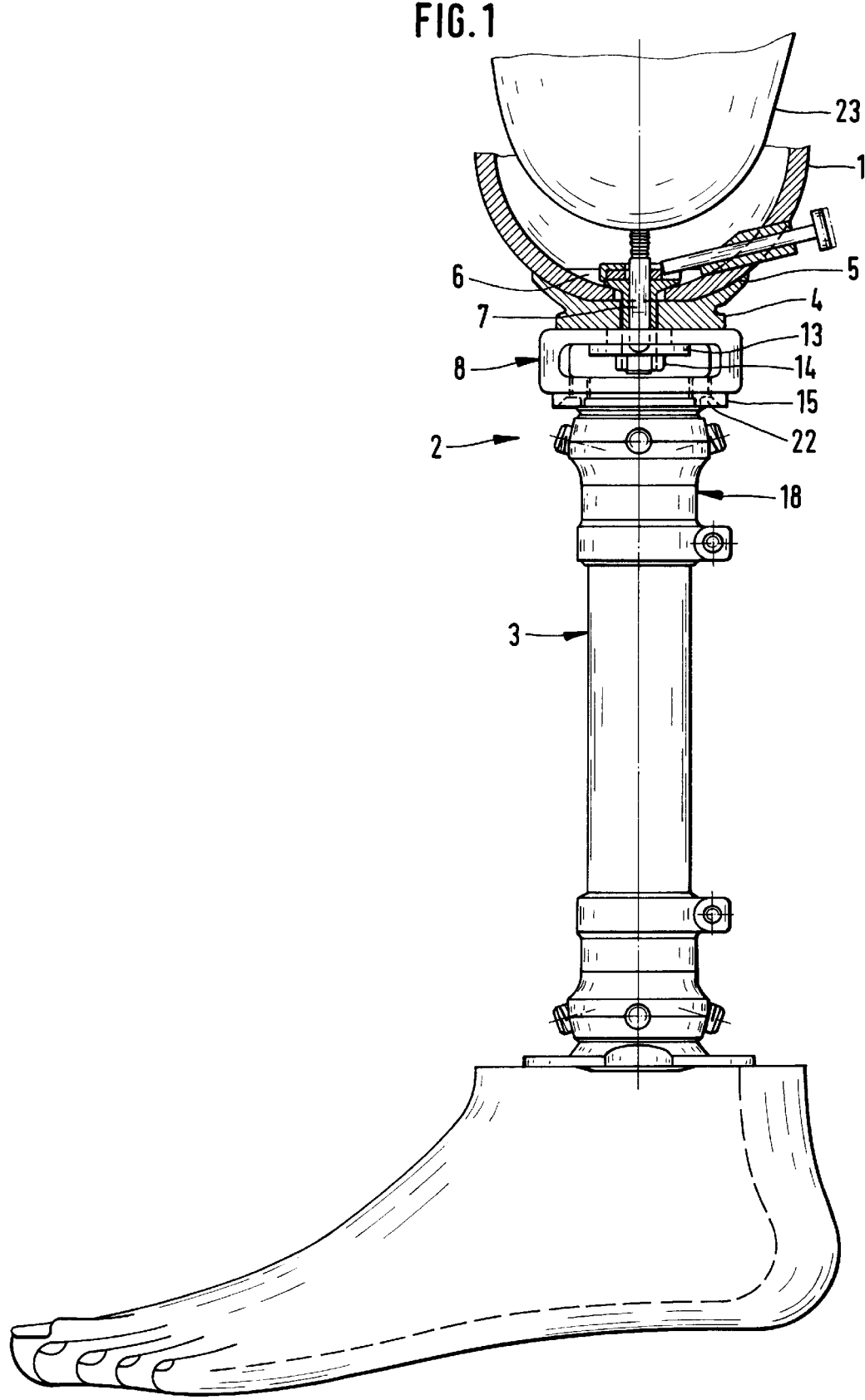
FIG. 1 is a sectional side view of a stump socket which is connected to a prosthetic limb through an alignment device.

As shown in FIG. 1 a stump socket 1 is connected to a prosthetic limb 3 by means of an alignment device 2.

The alignment device 2 comprises an attachment member 4 having a spherical portion 5 for receiving the stump socket 1 on its side facing the stump socket 1. The bottom inner surface of the stump socket is covered by a rounded clamping disc 6 which is formed to conform the spherical portion 5 and cooperates with the spherical portion 5 to clamp the liner therebetween. The side of the attachment member facing away from the spherical portion 5 is flat. The clamping disc 6 and the attachment member 4 both have a center bore for receiving a bolt serving as a hollow pin 7. An alignment member 8 formed as an intermediate member is provided adjacent to the side of the attachment member 4 opposite to the spherical portion 5. The alignment member is constructed as a cage having a top wall 9, side walls 10 and a bottom wall 11. The top wall 9 has an opening 12 which is considerably larger than the diameter of the hollow pin 7. A washer 13 is provided at the side of the top wall 9 facing the bottom wall 11. The outer dimensions of the washer 13 exceed the inner dimensions of the opening 12. A nut 14 to be screwed onto the bolt-shaped hollow pin 7 is arranged at the side of the washer 13 facing away from the top wall 9. The side walls 10 are dimensioned so that the spacing between the bottom wall 11 and the top wall 9 is greater than the axial length of the portion to be received of the hollow pin 7 including the washer and the nut. As shown in the figures at least one of the side walls has an aperture allowing to tighten or loosen the nut from outside by means of a wrench.

An adjustment member 15 having a flat upper surface is provided at the side of the bottom wall 11 facing away from the top wall 9. The lower side of the adjustment member 15 facing away from the intermediate member comprises a substantially spherically shaped surface 16 and a coaxially arranged truncated pyramidal nub 17. The adjustment member is connected to the alignment member 8 by means of screws 32. The nub is disposed to have the base of the truncated pyramid at its free end facing away from the intermediate member. A connection member 18 formed as a clamping adapter is disposed adjacent to the side having the truncated pyramidal nub 17. The side of the connection member 18 facing the truncated pyramidal nub comprises a recess having a spherical wall conforming the spherical surface 16. Four setting screws 19 having respective axes aligned perpendicular to the walls of the truncated pyramidal nub protrude into the recess from the outside.

At its opposite side the clamping adapter 18 has a bore with a slotted wall and a clamping ring 20. The bore is slightly larger than the outer diameter of a tubular member 21 of the prosthetic limb 3 to be fastened thereto. The size of the bore is chosen to produce a firm connection between the clamping member 18 and the tubular member 21 when tightening the clamping ring.

In operation the clamping disc 6 is inserted inside the stump socket 1, whereupon the stump socket 1 is placed onto the spherical portion 5 of the attachment member 4 and the bolt 7 is passed through the openings. The alignment member 8 formed as an intermediate member is now laterally displaced relative to the attachment member 4 so that the center axis of the bottom wall 11 is in the desired position relative to the center axis of the pin 7. Thereafter the position of the pin or bolt at the top wall 9 is fixed by tightening the nut 14. The adjustment member 15 is now (or has already been before) connected to the alignment member 8 by means of indicated screws 32 in such a manner that the center axis of the adjustment member 15 coincides with the center axis of the bottom wall 11. An angular adjustment of the adjustment member 15 relative to the connection member 18 can be made by suitable adjustment using the setting screws 19. The connection member 18 is firmly and coaxially connected to the tube 21 by means of the clamping ring 20.

Figure 4:
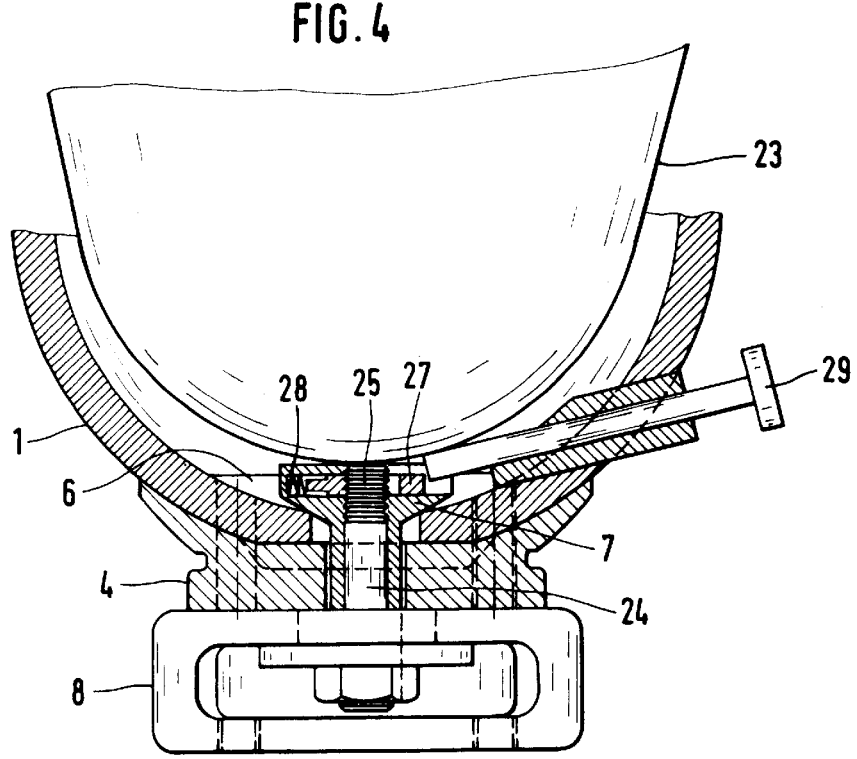
FIG. 4 is an enlarged representation of a detail of the first embodiment in locked position.
Figure 5:
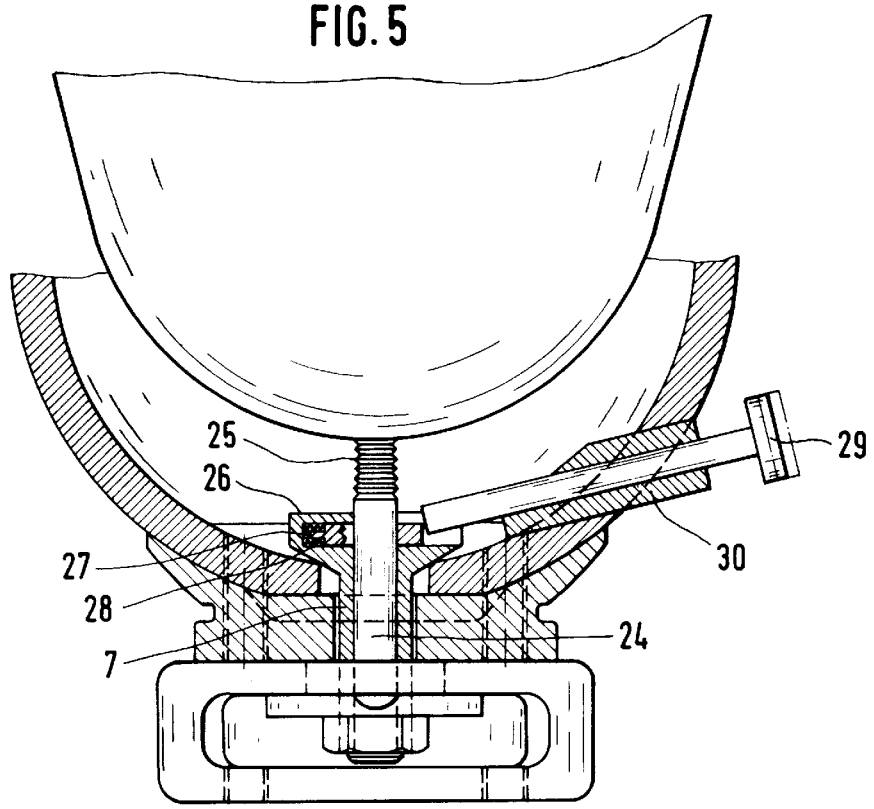
FIG. 5 shows the same detail in released condition.

As best shown in FIGS. 4 and 5 a liner covering the residual limb is received in the above-described device. This is achieved by a bolt 24 provided at the bottom center of the liner 23. The outer diameter of the bolt substantially corresponds to the inner diameter of the inner bore of the hollow pin 7, being slightly smaller to allow sliding displacement within the inner bore. In the embodiment shown the bolt 24 comprises a grooved or ratchet-shaped portion 25 immediately adjacent to the liner 23. The head 26 of the hollow pin 7 has a locking member therein, the locking member comprising a disc 27 extending perpendicular to the axis of symmetry of the hollow pin 7 and being biased in direction towards the axis of symmetry by means of a spring. The disc has a bore which is larger than the diameter of the bolt 24. A push pin 29 is disposed on the side of the disc opposite to the spring and supported in a guide member 30 to forceably engage the disc 27 in the manner shown in FIG. 5 and displace the disc from its advanced position shown in FIG. 4 into the retracted position shown in FIG. 5 against the spring force. Unless a force is exerted by the push pin 29 the disc 27 locks the bolt 24 in the inserted position by engagement with the grooved portion 25, as shown in FIG. 4. Whenever a force is exerted onto the push pin 29 the lock is released and the liner, together with the bolt, may be removed from the hollow pin 7 or inserted therein.

The embodiment shown in FIG. 3 differs from the above-described embodiment only in that the locking device is provided at the bottom of the attachment member 4 rather than within the head of the hollow pin 7. To this end a chamber is disposed at the bottom side of the attachment member 4. The chamber comprises a slot extending perpendicular to the longitudinal axis of symmetry of the device. As in the above embodiment a disc 27' formed as a slider is provided in the slit and urged towards the central axis by means of a spring 28. As before a push pin 29 acts upon the disc for pushing back the slider-shaped disc 27 from biased locking position, which corresponds to the position shown in FIG. 4, into the released position corresponding to that of FIG. 5. The hollow pin 7' differs from the first embodiment in that it comprises an aperture 31. The slider-shaped disc 27 extends inwardly through the aperture 31 and lockingly engages a grooved portion 25' of the bolt 24' provided at the corresponding elevation thereof.

Figure 6:
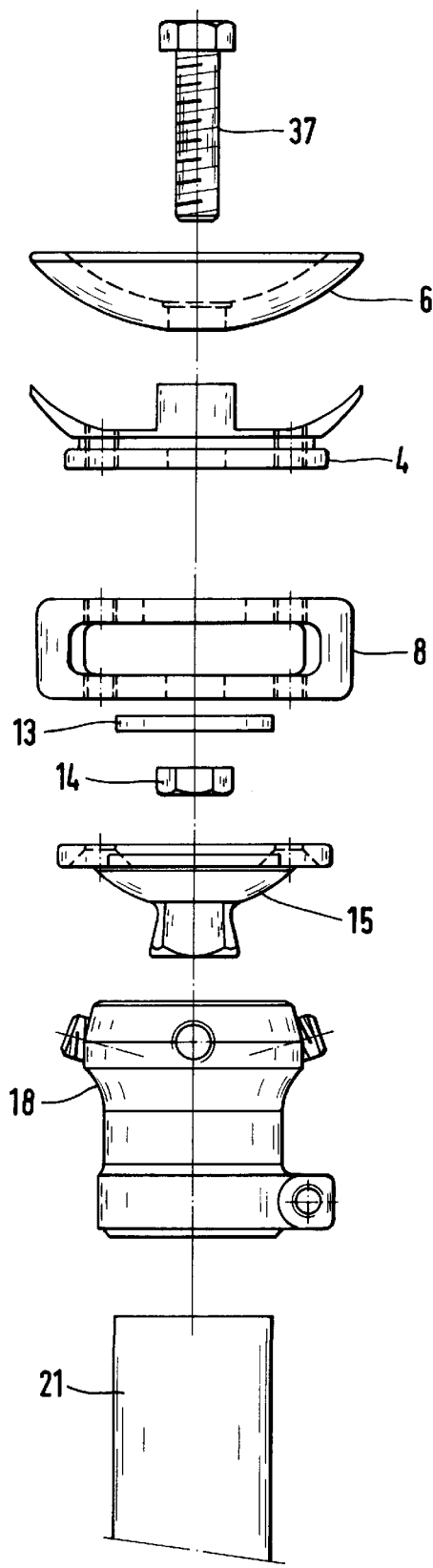
FIG. 6 is an exploded representation of a modified embodiment.

The embodiment of FIG. 6 differs from the previous embodiments merely by providing a usual screw bolt 37 in place of the hollow pin 7 receiving the bolt 24.

Figure 7:
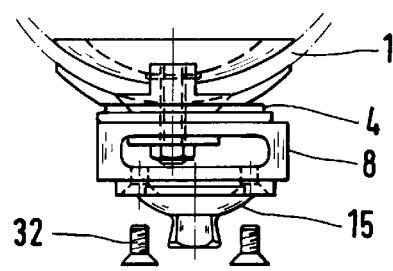
FIG. 7 shows a detail of the apparatus.

FIG. 7 shows a position of the previously described embodiments whereby the stump socket 1 is laterally offset with respect to the alignment member 8 connected to the prosthetic limb.

What is claimed is:

1. A device comprising:

a stump socket; and an alignment device for connecting the stump socket to a prosthetic limb;

the alignment device comprising an alignment member having an opening receiving a pin mounted to the stump socket, whereby the size of the opening is substantially greater than the cross-sectional diameters of the pin and the pin can be locked in any position within the opening, wherein the pin is a hollow pin for receiving a bolt connected to a liner to be received, and wherein a locking device is provided for locking the bolt within the hollow pin at a predetermined position.

2. Alignment device according to claim 1, further comprising an attachment member (4) having a center bore receiving the pin (7, 7') and having a diameter which substantially corresponds to that of the pin, the attachment member (4) being connectable to the alignment member (8) in various relative positions in a transverse and longitudinal direction.

3. Alignment device according to claim 2, wherein the attachment member (4) comprises a spherical portion (5) provided at its side facing away from the alignment member (8) and arranged coaxially to the center bore.

4. Alignment device according to claim 3, further comprising a clamping disc (6) cooperating with the spherical portion (5).

5. Alignment device according to any of the claims 1 to 4, wherein a washer (13) having a bore for receiving the pin is provided at the side of the alignment member (8) opposite to the stump socket (1) to be received, the washer having a diameter which is larger than the size of the opening (12), a nut (14) engaging the pin (7, 7') being disposed adjacent to the washer (13) at its side opposite to the stump socket (1).

6. Alignment device according to claim 5, further comprising an additional connecting member (15) having one side thereof adapted for connection to the prosthetic limb (21) and the other side thereof pivotally connected to the alignment member (8) to swing within a range defined by a cone angle around the center axis of the connecting member (15).

7. Alignment device according to claim 6, wherein the connecting member (15) comprises a clamping device (20) for connection to the prosthetic limb (21).

* * * * *